US010729872B2

(12) United States Patent
Okita

(10) Patent No.: US 10,729,872 B2
(45) Date of Patent: Aug. 4, 2020

(54) DRIVING METHOD FOR METERING PUMP, DRIVING APPARATUS FOR METERING PUMP, VAPORIZER, AND ANESTHESIA APPARATUS

(71) Applicant: ACOMA MEDICAL INDUSTRY CO., LTD., Bunkyo-ku, Tokyo (JP)

(72) Inventor: Kazunari Okita, Tokyo (JP)

(73) Assignee: ACOMA MEDICAL INDUSTRY CO., LTD, Tokyo (JP)

( * ) Notice: Subject to any disclaimer, the term of this patent is extended or adjusted under 35 U.S.C. 154(b) by 0 days.

(21) Appl. No.: 15/022,153

(22) PCT Filed: Sep. 24, 2015

(86) PCT No.: PCT/JP2015/076884
§ 371 (c)(1),
(2) Date: Mar. 15, 2016

(87) PCT Pub. No.: WO2016/143173
PCT Pub. Date: Sep. 15, 2016

(65) Prior Publication Data
US 2018/0001040 A1    Jan. 4, 2018

(30) Foreign Application Priority Data
Mar. 9, 2015 (JP) .................. 2015-046159

(51) Int. Cl.
*A61M 16/18* (2006.01)
*B01F 15/02* (2006.01)
(Continued)

(52) U.S. Cl.
CPC ........ *A61M 16/18* (2013.01); *A61M 16/0057* (2013.01); *A61M 16/01* (2013.01);
(Continued)

(58) Field of Classification Search
CPC ...... A61M 16/00; A61M 16/01; A61M 16/10; A61M 16/12; A61M 16/18; A61M 16/104;
(Continued)

(56) References Cited

U.S. PATENT DOCUMENTS 3,168,872 A * 2/1965 Pinkerton ................ F04B 7/06
417/492
4,770,168 A * 9/1988 Rusz ..................... A61M 16/18
128/203.12
(Continued)

FOREIGN PATENT DOCUMENTS

| JP | 02064273 A * | 3/1990 |
| JP | 2001263256 A | 9/2001 |
| JP | 2012032187 A | 9/2001 |

OTHER PUBLICATIONS

Practical anesthesia Machine with Electronic Anesthetic Gas Delivery System, The Japanese journal of medical instrumentation, vol. 69, No. 8 (1999).

*Primary Examiner* — Colin W Stuart
(74) *Attorney, Agent, or Firm* — Arent Fox LLP

(57) ABSTRACT

A metering pump is joined to the stepping motor, includes an eccentric mechanism converting a revolving motion of the stepping motor into a reciprocating motion of a plunger, and makes a constant liquid delivery by sucking and discharging an anesthetic agent through variations in the cubic volume of a cylinder caused by the reciprocating motion of the plunger. The control section: calculates a suction and discharge cycle T of the metering pump on the basis of a set anesthetic-gas concentration and a fresh-gas flow rate; sets a discharge period T2 of the cycle T to be longer than a suction period T1 of the cycle T; and controls the revolution speed of the (Continued)

stepping motor so that the travelling speed of the plunger is kept constant during the discharge period T2.

7 Claims, 6 Drawing Sheets

(51) Int. Cl.
    *B01F 15/04*     (2006.01)
    *B01F 3/02*     (2006.01)
    *F04B 13/00*     (2006.01)
    *F04B 11/00*     (2006.01)
    *F04B 9/04*     (2006.01)
    *F04B 49/20*     (2006.01)
    *A61M 16/10*     (2006.01)
    *A61M 16/12*     (2006.01)
    *A61M 16/14*     (2006.01)
    *F04B 9/02*     (2006.01)
    *F04B 9/00*     (2006.01)
    *F04B 7/04*     (2006.01)
    *A61M 16/00*     (2006.01)
    *A61M 16/01*     (2006.01)

(52) U.S. Cl.
    CPC .......... *A61M 16/10* (2013.01); *A61M 16/104* (2013.01); *A61M 16/12* (2013.01); *A61M 16/14* (2013.01); *B01F 3/02* (2013.01); *B01F 15/02* (2013.01); *B01F 15/04* (2013.01); *F04B 7/04* (2013.01); *F04B 9/00* (2013.01); *F04B 9/02* (2013.01); *F04B 9/04* (2013.01); *F04B 11/0041* (2013.01); *F04B 13/00* (2013.01); *F04B 49/20* (2013.01); *A61M 16/186* (2013.01); *A61M 2016/0033* (2013.01); *A61M 2016/0039* (2013.01); *A61M 2205/3365* (2013.01); *A61M 2205/3653* (2013.01); *A61M 2205/502* (2013.01); *A61M 2205/6054* (2013.01); *F04B 2201/0202* (2013.01); *F04B 2203/0209* (2013.01)

(58) Field of Classification Search
    CPC .. A61M 2016/0033; A61M 2205/3365; A61M 16/0057; A61M 16/14; A61M 16/183; A61M 2016/3365; A61M 1/0066; A61M 1/1081; B01F 3/02; B01F 15/02; B01F 15/04; F04B 9/00; F04B 9/02; F04B 9/04; F04B 11/0041; F04B 13/00; F04B 19/00; F04B 19/22; F04B 7/04; F04B 7/06

See application file for complete search history.

(56) References Cited

U.S. PATENT DOCUMENTS

| | | | | |
|---|---|---|---|---|
| 5,022,831 | A * | 6/1991 | Gerlach | F04B 7/06 417/500 |
| 5,242,403 | A * | 9/1993 | Falb | A61M 16/18 128/204.15 |
| 5,246,354 | A * | 9/1993 | Pardinas | F04B 7/06 417/493 |
| 5,863,187 | A * | 1/1999 | Bensley | F04B 1/324 417/218 |
| 9,057,363 | B2 * | 6/2015 | Capone | F04B 7/00 |
| 2003/0104634 | A1 * | 6/2003 | Jacobs | B01L 3/0289 436/180 |
| 2012/0318263 | A1 * | 12/2012 | Jones | A61M 16/01 128/203.12 |

* cited by examiner

DRIVING METHOD FOR METERING PUMP, DRIVING APPARATUS FOR METERING PUMP, VAPORIZER, AND ANESTHESIA APPARATUS

CROSS-REFERENCE TO RELATED APPLICATIONS

This application is a National Stage entry of International Application No. PCT/JP2015/076884, filed Sep. 24, 2015, which claims priority to Japanese Patent Application No. 2015-046159, filed Mar. 9, 2015. The disclosure of the priority applications are incorporated in their entirety herein by reference.

The present invention relates to a driving method for a metering pump and a driving apparatus for a metering pump. Also provided are a vaporizer, and an anesthesia apparatus. Particularly, it relates to a driving method for a metering pump and a driving apparatus for a metering pump which are capable of suppressing a pulsation in the metering pump, and lowering the costs and reducing the sizes of associated vaporizers and anesthesia apparatus.

BACKGROUND ART

FIG. 5(a) shows the configuration of a conventional anesthesia apparatus (refer to Non-Patent Document 1). In FIG. 5(a), the anesthesia apparatus includes: an operation section 51, a control section 52, an anesthetic agent bottle 53, a motor driver 54, a stepping motor 55, a metering pump 56, a vaporizing chamber 59, an anesthetic-agent identifying sensor 61, an anesthetic-agent detecting sensor 62 and a fresh-gas flow-rate sensor 63. An anesthetic agent is stored in the anesthetic agent bottle 53 and is sent through an anesthetic-agent flow path 71 to the suction port of the metering pump 56. A fresh gas is a mixture of oxygen, a nitrous oxide and air and is supplied through a gas pipe line 75 to the vaporizing chamber 59.

Upon setting an anesthetic gas concentration in the operation section 51, the control section 52 calculates a required volume of an anesthetic gas (gaseous matter) on the basis of the set anesthetic-gas concentration value and a fresh-gas flow rate detected by the fresh-gas flow-rate sensor 63. On the basis of Avogadro's law, the control section 52 converts the volume of the anesthetic gas (gaseous matter) into a volume of an anesthetic agent (liquid matter). In order to allow the metering pump 56 to discharge the calculated volume of anesthetic agent, the control section 52 regulates the revolution speed of the motor 55 via the motor driver 54. From the metering pump 56, the anesthetic agent is discharged in the fixed volume corresponding to the set anesthetic-gas concentration value. Then, the anesthetic agent is delivered through a flow path 72 to the vaporizing chamber 59, and in the vaporizing chamber 59, the anesthetic agent is mixed with the fresh gas. This operation is continuously executed, and thereby, even if the set anesthetic-gas concentration value or the fresh-gas flow rate is varied, then the variation is followed by a real-time variation in the volume of liquid delivered from the metering pump 56.

In the conventional anesthesia apparatus, the metering pump 56 needs to deliver a predetermined volume of liquid precisely at an extremely-low flow rate in units of microns. In order to make such a liquid delivery, a metering pump (e.g., see FIGS. 1(a) to 1(d)) is employed which: is driven by the stepping motor 55; includes an eccentric mechanism converting a revolving motion of the stepping motor 55 into a reciprocating motion of a plunger of the metering pump; and makes a constant liquid delivery by sucking and discharging a liquid through variations in the cubic volume of a cylinder of the metering pump caused by the reciprocating motion of the plunger.

When the stepping motor 55 revolves at a constant speed, the reciprocating motion of the plunger in the axial directions becomes a substantially sinusoidal reciprocating motion. Accordingly, as shown in FIG. 5(b), the temporary variation in the suction volume and discharge volume of the metering pump traces a sinusoidal transition. Consequently, during the discharge period, an anesthetic agent is delivered such that the discharge volume varies in a sinusoidal form with time, thereby giving a pulsation to the discharge volume of the metering pump. As shown in FIG. 5(c), the effect of the pulsation remains even though in the vaporizing chamber 59, the anesthetic agent vaporizes gradually to smooth the temporary variation in the anesthetic gas concentration.

FIG. 6(a) shows a result of gas concentration measurements where the anesthetic-gas concentration value is set to 1.0[%] and the fresh-gas flow rate is varied in accordance with the periods: it is 0.5 [L/min] during a period of Y0 to Y1, 1.0 [L/min] during a period of Y1 to Y2 and 6.0 [L/min] during a period of Y2 to Y3. A conspicuous pulsation appears during the period Y0-Y1 when the fresh-gas flow rate is relatively low. Then, the pulsation amplitude lowers during the period Y1-Y2 when the fresh-gas flow rate is doubled, and further, the pulsation becomes almost inconspicuous during the period Y2-Y3 when the fresh-gas flow rate is much higher. In short, the effect of a pulsation appears conspicuously when the fresh-gas flow rate is low and the revolution speed of the metering pump 56 (stepping motor 55) is relatively low.

As described above, a metering pump has the problem of a pulsation, and hence, measures to solve the problem have been taken in various fields including an anesthesia apparatus. For example, Patent Document 1 and Patent Document 2 disclose a technical method in which a plurality of plunger pumps are joined together to adjust the total discharge flow rate to a fixed value.

The document JPH0264273A and US2004/151594A1 disclose plungers having cylindrical pistons which move up and down within a cylinder.

PRIOR ART DOCUMENTS

Patent Documents

Patent Document 1: Japanese Patent Laid-Open Publication No. 2012-32187
Patent Document 2: Japanese Patent Laid-Open Publication No. 2001-263253
Non-Patent Document 1: Kazunari Okita; "Practical anesthesia Machine with Electronic Anesthetic Gas Delivery System", The Japanese journal of medical instrumentation Vol. 69, No. 8 (1999)

SUMMARY OF THE INVENTION

Problems to be Solved by the Invention

However, the technical method of Patent Document 1 and Patent Document 2 in which a plurality of plunger pumps are joined together to adjust the total discharge flow rate to a fixed value may increase the cost of the anesthesia apparatus, or complicate the control thereof.

Furthermore, in the field of an anesthesia apparatus, there is a technical method of suppressing a pulsation when the revolution speed of the stepping motor 55 (15) is relatively low, in other words, when the set anesthetic-gas concentration value is small, or when the fresh-gas flow rate is low. As shown in FIG. 5(a), the vaporizing chamber 59 is arranged at the place where an anesthetic agent is mixed with a fresh gas, and the anesthetic agent is gradually vaporized there to smooth the pulsation. However, the vaporizing chamber 59 requires a relatively large cubic volume, thereby hindering a reduction in the size of the anesthesia apparatus.

In addition, the configuration including the vaporizing chamber 59 raises the following problems. Firstly, when a change is made in the set anesthetic-gas concentration value, the anesthetic gas produced based on the previous set anesthetic-gas concentration value remains in the vaporizing chamber 59. Accordingly, before the carrier-gas flow rate is equilibrated with the vaporization rate in the vaporizing chamber 59, a time lag arises until the anesthetic gas concentration stabilizes. In the example of FIG. 6(b), a time lag Ttb arises when the set anesthetic-gas concentration value is changed to a smaller value, while a time lag Tbt arises when the set anesthetic-gas concentration value is changed to a larger value.

Secondly, if the fresh-gas flow rate is sharply changed, as shown in FIG. 6(c), an overshoot or undershoot arises in the anesthetic gas concentration. Specifically, if the fresh-gas flow rate is sharply lowered at a time Y5 in FIG. 6(c), then before the anesthetic agent remaining in the vaporizing chamber 59 vaporizes, the anesthetic gas concentration overshoots temporarily from the set value thereof. On the other hand, if the fresh-gas flow rate is sharply heightened at a time Y6 in FIG. 6(c), then before a certain volume of the anesthetic agent accumulates in the vaporizing chamber 59, the anesthetic gas concentration undershoots temporarily from the set value thereof.

None of the above time lag, overshoot and undershoot would seriously hinder the operation of an anesthesia apparatus. However, they could raise some problems such as lengthening the time taken to regulate anesthesia.

Therefore, it is an object of the present invention to provide a driving method for a metering pump, and a driving apparatus for a metering pump which are capable of suppressing a pulsation in the metering pump without increasing the cubic volume of an anesthesia apparatus, and lowering the costs and reducing the sizes of vaporizers and anesthesia apparatus.

Means for Solving the Problems

In order to solve the problems, a driving method for a metering pump is provided, which includes an eccentric mechanism converting a revolving motion of a motor into a reciprocating motion of a plunger of the metering pump, and makes a constant liquid delivery by sucking and discharging a liquid through variations in the cubic volume of a cylinder of the metering pump caused by the reciprocating motion of the plunger, wherein a discharge period of the metering pump is set to be longer than a suction period of the metering pump, and the revolution speed of the motor is controlled so that the travelling speed of the plunger is kept constant during the discharge period.

In some embodiments, during the discharge period of the metering pump, to vary the revolution speed of the motor in a sinusoidal form at intervals of a predetermined angle so that the motor makes a sinusoidal revolving motion.

In a further aspect of the invention there is provided a driving apparatus for a metering pump The driving apparatus comprises: a motor; a control section controlling the revolution of the motor; and a metering pump joined to the motor, the metering pump including an eccentric mechanism converting a revolving motion of the motor into a reciprocating motion of a plunger of the metering pump, and making a constant liquid delivery by sucking and discharging a liquid through variations in the cubic volume of a cylinder of the metering pump caused by the reciprocating motion of the plunger, wherein the control section sets a discharge period of the metering pump to be longer than a suction period of the metering pump, and controls the revolution speed of the motor so that the travelling speed of the plunger is kept constant during the discharge period.

In some embodiments, during the discharge period of the metering pump, the control section varies the revolution speed of the motor in a sinusoidal form at intervals of a predetermined angle so that the motor makes a sinusoidal revolving motion.

In some embodiments, the motor is a stepping motor which is controlled with Np drive pulses within a rotation-angle range of 0 to π during the discharge period of the metering pump; and the control section supplies the (k)th (k=1 to Np) drive pulse at a timing $t_k$ defined by the following formula during the discharge period of the metering pump if the reciprocating motion of the plunger is Vp.

$$t_k = \frac{\pi}{NpVp}\sum_{m=1}^{k}\sin\left(\frac{m\pi}{Np}\right)$$ [Numerical Formula 1]

Also provided is a vaporizer which comprises: a motor; a control section controlling the revolution of the motor; a metering pump joined to the motor, the metering pump including an eccentric mechanism converting a revolving motion of the motor into a reciprocating motion of a plunger of the metering pump, and making a constant liquid delivery by sucking and discharging a liquid through variations in the cubic volume of a cylinder of the metering pump caused by the reciprocating motion of the plunger; a gas pipe line transferring a fresh gas; and a flow path connected to the gas pipe line, the flow path delivering and vaporizing the liquid discharged from the metering pump and supplying the liquid to the gas pipe line, in which the vaporizer leads out a mixed gas of the fresh gas and the vaporized liquid gas, wherein the control section calculates a suction and discharge cycle of the metering pump on the basis of a set concentration of the mixed gas and a set flow rate of the fresh gas, sets a discharge period of the cycle to be longer than a suction period of the cycle, and controls the revolution speed of the motor so that the travelling speed of the plunger is kept constant during the discharge period.

In the vaporizer, during the discharge period of the metering pump, the control section varies the revolution speed of the motor in a sinusoidal form at intervals of a predetermined angle so that the motor makes a sinusoidal revolving motion.

In the vaporizer discussed above, the motor is a stepping motor which is controlled with Np drive pulses within a rotation-angle range of 0 to π during the discharge period of the metering pump; and the control section supplies the (k)th (k=1 to Np) drive pulse at a timing $t_k$ defined by the following formula during the discharge period of the metering pump if the reciprocating motion of the plunger is Vp.

$$t_k = \frac{\pi}{NpVp}\sum_{m=1}^{k} \sin\left(\frac{m\pi}{Np}\right)$$ [Numerical Formula 1]

In the vaporizer discussed above, a flow-rate detecting means for detecting a flow rate of the fresh gas is provided, the flow-rate detecting means being arranged before the junction place of the gas pipe line with the flow path in the transfer direction of the fresh gas; and the control section calculates a suction and discharge cycle of the metering pump on the basis of a set concentration of the mixed gas and a flow rate of the fresh gas detected by the flow-rate detecting means.

In the vaporizer discussed above, the anesthesia apparatus outputs, as an anesthetic gas, a mixed gas of a fresh gas containing at least oxygen and an anesthetic agent gas subjected to vaporization.

Advantages of the Invention

In some embodiments, a discharge period of the metering pump is set to be longer than a suction period thereof. Therefore, the suction period when no discharge is given is shortened to the utmost, thereby suppressing a fall in the discharge flow rate of the metering pump. Besides, the revolution speed of the motor is controlled so that the travelling speed of the plunger is kept constant during the discharge period. Therefore, the discharge flow rate of the metering pump is kept substantially constant, thereby suppressing a pulsation in the metering pump.

In some embodiments, during the discharge period of the metering pump, the revolution speed of the motor is varied in a sinusoidal form at intervals of a predetermined angle so that the motor can make a sinusoidal revolving motion. Therefore, the travelling speed of the plunger is kept constant to keep constant the discharge flow rate of the metering pump, thereby suppressing a pulsation in the discharge flow rate of the metering pump.

In addition, the driving method for the metering pump or the driving apparatus for the metering pump is applied to a vaporizer and an anesthesia apparatus, thereby dispensing with a vaporizing chamber conventionally necessary for suppressing a pulsation in the metering pump. This makes it feasible to suppress a pulsation in the metering pump without increasing the cubic volumes of the vaporizer and the anesthesia apparatus, and to lower the costs and reduce the sizes of the vaporizer and the anesthesia apparatus.

In some embodiments, the control section calculates a suction and discharge cycle of the metering pump on the basis of a set concentration of the mixed gas and a flow rate of the fresh gas, and sets a discharge period of the cycle to be longer than a suction period of the cycle. Therefore, the suction period when no discharge is given is shortened to the utmost, thereby suppressing a fall in the concentration of the mixed gas. Further, the revolution speed of the motor is controlled so that the travelling speed of the plunger is kept constant during the discharge period. Therefore, the discharge flow rate of the metering pump is kept substantially constant, thereby suppressing a pulsation in the metering pump. As a result, a vaporizing chamber conventionally necessary for suppressing the pulsation is dispensable, thereby making it feasible to suppress a pulsation in the metering pump without increasing the cubic volume of the vaporizer, and to lower the cost and reduce the size of the vaporizer. Still further, since a vaporizing chamber is unnecessary, a time lag will not arise when the set mixed-gas concentration has been changed, and an overshoot or undershoot in the mixed gas concentration will not arise when the fresh-gas flow rate has been sharply changed.

In some embodiments, during the discharge period of the metering pump, the revolution speed of the motor is varied in a sinusoidal form at intervals of a predetermined angle so that the motor can make a sinusoidal revolving motion. Therefore, the travelling speed of the plunger is kept constant to keep constant the discharge flow rate of the metering pump, thereby suppressing a pulsation in the discharge flow rate of the metering pump.

In some embodiments, the control section calculates a suction and discharge cycle of the metering pump on the basis of a set concentration of the anesthetic gas and a flow rate of the fresh gas, and sets a discharge period of the cycle to be longer than a suction period of the cycle. Therefore, the suction period when no discharge is given is shortened to the utmost, thereby suppressing a fall in the concentration of the mixed gas. Further, the revolution speed of the motor is controlled so that the travelling speed of the plunger is kept constant during the discharge period. Therefore, the discharge flow rate of the metering pump is kept substantially constant, thereby suppressing a pulsation in the metering pump. As a result, a vaporizing chamber conventionally necessary for suppressing the pulsation is dispensable, thereby making it feasible to suppress a pulsation in the metering pump without increasing the cubic volume of the anesthesia apparatus, and to lower the cost and reduce the size of the anesthesia apparatus. Still further, since a vaporizing chamber is unnecessary, a time lag will not arise when the set concentration of the mixed gas has been changed, and an overshoot or undershoot in the anesthetic gas concentration will not arise when the fresh-gas flow rate has been sharply changed.

MODE FOR CARRYING OUT THE INVENTION

An embodiment of the present invention will be below described with reference to the drawings. First of all, a driving apparatus and a driving method for a metering pump 16 according to the embodiment of the present invention will be described with reference to FIGS. 1(a) to 1(f).

Figure 1:
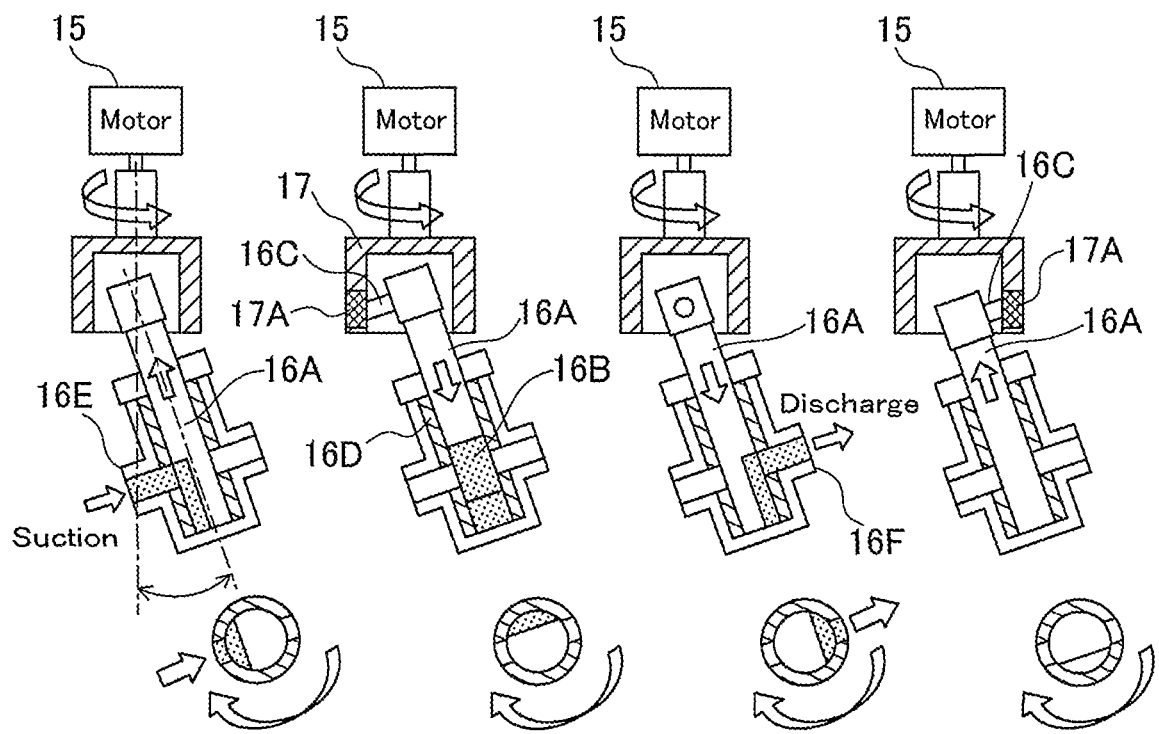
FIGS. 1(a) to 1(f) are illustrations showing an operation of a driving apparatus for a metering pump according to an embodiment of the present invention.

FIGS. 1(a) to 1(f) show an operation of the driving apparatus for the metering pump 16. FIGS. 1(a) to 1(d)

schematically show a structure of the metering pump 16: sectional views of the metering pump 16 along the axial directions of a plunger 16A and sectional views of the metering pump 16 along the directions perpendicular to the axis of the plunger 16A. FIG. 1(e) is a time chart showing a suction period and a discharge period of the metering pump 16 and FIG. 1(f) is a time chart showing drive pulses of a stepping motor 15 which are outputted by a motor driver 14.

In this embodiment likewise, the metering pump 16 is a metering pump conventionally employed for an anesthesia apparatus. The metering pump 16 is driven by the stepping motor 15, includes an eccentric mechanism converting a revolving motion of the stepping motor 15 into a reciprocating motion of the plunger 16A, and makes a constant liquid delivery by sucking and discharging a liquid through variations in the cubic volume of a cylinder 16D caused by the reciprocating motion of the plunger 16A. Specifically, the metering pump 16 is a valve-less plunger pump having the structure shown in FIGS. 1(a) to 1(d).

In FIGS. 1(a) to 1(d), a cylindrical crank 17 is attached to the revolving shaft of the stepping motor 15, and to the crank 17, a pin 16C attached to the plunger 16A is connected via a bearing 17A. The axis of the plunger 16A is arranged at a specified angle to the revolution axis of the stepping motor 15 (crank 17). The stepping motor 15 is driven to revolve the crank 17 and shift the position of the pin 16C, and thereby, the plunger 16A revolves while making a reciprocating motion inside of the cylinder 16D. The travelling range of the plunger 16A in the axial directions varies in accordance with the angle to the revolution axis of the stepping motor 15, so that by adjusting this angle, the discharge volume of the metering pump 16 can be optionally set.

The plunger 16A has a notch portion 16B located in the end part (on the side opposite to the crank 17) of the plunger 16A, so that the plunger 16A itself can open and close a suction port 16E and a discharge port 16F. This structure dispenses with a valve.

FIG. 1(a) shows the metering pump 16 during the suction period, specifically at the time when the stepping motor 15 has revolved by $\pi/2$ from the start of the suction period. This indicates that the notch portion 16B of the plunger 16A faces toward the suction port 16E, and simultaneously, the plunger 16A moves toward the crank 17 in the axial directions and sucks an anesthetic agent (liquid).

FIG. 1(b) shows the metering pump 16 at the end of the suction period (when the stepping motor 15 has revolved by $\pi$ from the start of the suction period). This indicates that the notch portion 16B of the plunger 16A faces forward in the figure to close the suction port 16E. FIG. 1(b) also shows the metering pump 16 at the start of the discharge period.

FIG. 1(c) shows the metering pump 16 during the discharge period, specifically at the time when the stepping motor 15 has revolved by $\pi/2$ from the start of the discharge period. This indicates that the notch portion 16B of the plunger 16A faces toward the discharge port 16F, and simultaneously, the plunger 16A moves toward the opposite side to the crank 17 in the axial directions and discharges the anesthetic agent (liquid).

FIG. 1(d) shows the metering pump 16 at the end of the discharge period (when the stepping motor 15 has revolved by $\pi$ from the start of the discharge period). This indicates that the notch portion 16B of the plunger 16A faces backward in the figure to close the discharge port 16F. FIG. 1(d) also shows the metering pump 16 at the start of the suction period.

In the driving apparatus for the metering pump 16 of this embodiment, as shown in FIG. 1(e), the discharge period is set to be longer than the suction period of the metering pump 16. FIG. 1(e) indicates a timing Ta corresponding to FIG. 1(a); a timing Tb, FIG. 1(b); a timing Tc, FIG. 1(c); and a timing Td, FIG. 1(d).

As shown in FIG. 1(f), the stepping motor 15 revolves at a constant speed during the suction period of the metering pump 16, while the stepping motor 15 revolves at variable speeds during the discharge period thereof so that the plunger 16A can travel at a constant speed in the axial directions.

Specifically, a rotation angle $\Delta\theta$ per pulse or a step angle of the stepping motor 15 is determined, and the rotation angle of the stepping motor 15 is $\pi$ during a suction period T1 or a discharge period T2 of the metering pump 16. Consequently, the number of pulses Np necessary for the suction period T1 or the discharge period T2 is calculated in the formula "Np=$\pi/\Delta\theta$".

Accordingly, during the suction period T1 when the stepping motor 15 revolves at a constant speed, drive pulses may be given at a pulse interval of "T1/Np".

Next, during the discharge period T2 when the plunger 16A travels at a constant speed in the axial directions, drive pulses are given at irregular pulse intervals. A description will be below given about the timing for supplying drive pulses during the discharge period T2.

As described above, the stepping motor 15 is characterized in that "when the stepping motor 15 revolves at a constant speed, the plunger 16A makes a sinusoidal reciprocating motion in the axial directions". If the rotation angle and revolution speed of the stepping motor 15 are $\theta$ and $V_\theta$ respectively and the travelling speed of the plunger 16A in the axial directions is Vp, then the travelling speed vp of the plunger 16A in the axial directions is expressed as the following formula.

$Vp = V_\theta \sin\theta$

Hence, in order to keep constant the travelling speed Vp of the plunger 16A in the axial directions, the revolution speed $V_\theta$ of the stepping motor 15 needs to be set so as to satisfy the following formula.

$V\theta = Vp/\sin\theta$

On the other hand, as described above, if the number of pulses necessary for the rotation angle $\pi$ is Np, then the rotation angle $\Delta\theta$ per pulse of the stepping motor 15 is "$\Delta\theta=\pi/Np$". Hence, if an arbitrary pulse interval during the discharge period T2 is A, then a motor revolution speed $V_{\Delta\theta}$ is expressed as the following formula.

$$V_{\Delta\theta} = \pi/(A \cdot Np) \qquad (1)$$

Hence, in order to equate the motor revolution speed $V_{\Delta\theta}$ expressed as the formula (1) with the revolution speed $V_\theta$, the pulse interval A needs to be set so as to satisfy the following formula.

$$A = \pi \sin\theta/(Np \cdot Vp) \qquad (2)$$

If the timing for supplying each drive pulse during the discharge period T2 is t ($0 < t \le T2$), then a timing $t_1$ for supplying the first drive pulse is expressed as the following formula.

$$t_1 = \frac{\pi \sin\left(\frac{\pi}{Np}\right)}{NpVp} \qquad \text{[Numerical Formula 2]}$$

Similarly, a timing $t_2$ for supplying the second drive pulse is expressed as the following formula.

[Numerical Formula 3]

$$t_2 = \frac{\pi \sin\left(\frac{\pi}{Np}\right)}{NpVp} + \frac{\pi \sin\left(\frac{2\pi}{Np}\right)}{NpVp}$$

Hence, a timing $t_k$ for supplying the (k)th drive pulse is expressed as the following general formula.

[Numerical Formula 1]

$$t_k = \frac{\pi}{NpVp} \sum_{m=1}^{k} \sin\left(\frac{m\pi}{Np}\right) \quad (3)$$

Specifically, the timing $t_k$ for supplying the (k)th drive pulse during the discharge period T2 is given by the formula (3), and during the discharge period T2, the (k)th drive pulse is supplied to the stepping motor 15 at the timing $t_k$ defined by the formula (3). In the formula (3), the travelling speed Vp is a constant which is separately calculated in (the distance by which the plunger 16A travels inside of the cylinder 16D during the discharge period T2)/T2.

As described above, during the discharge period T2 of the metering pump 16, the revolution speed of the stepping motor 15 is varied in a sinusoidal form at intervals of a step angle (predetermined angle) so that the stepping motor 15 can make a sinusoidal revolving motion. Therefore, the travelling speed of the plunger 16A in the axial directions is kept constant, thereby keeping constant the discharge flow rate of the metering pump 16.

In the driving apparatus and the driving method for the metering pump 16 of this embodiment, the discharge period T2 of the metering pump 16 is set to be longer than the suction period T1. Therefore, the suction period T1 when no discharge is given is shortened to the utmost, thereby suppressing a fall in the discharge flow rate of the metering pump 16. Further, the stepping motor 15 revolves at variable speeds during the discharge period T2 so that the plunger 16A can travel at a constant speed in the axial directions. Therefore, the discharge flow rate of the metering pump 16 is kept constant, thereby suppressing a pulsation in the metering pump 16. Still further, the driving apparatus for the metering pump 16 is applied to a vaporizer and an anesthesia apparatus, thereby dispensing with a vaporizing chamber conventionally necessary for suppressing a pulsation in the metering pump 16. This makes it feasible to suppress a pulsation in the metering pump without increasing the cubic volumes of the vaporizer and the anesthesia apparatus, and to lower the costs and reduce the sizes of the vaporizer and the anesthesia apparatus.

Figure 2:
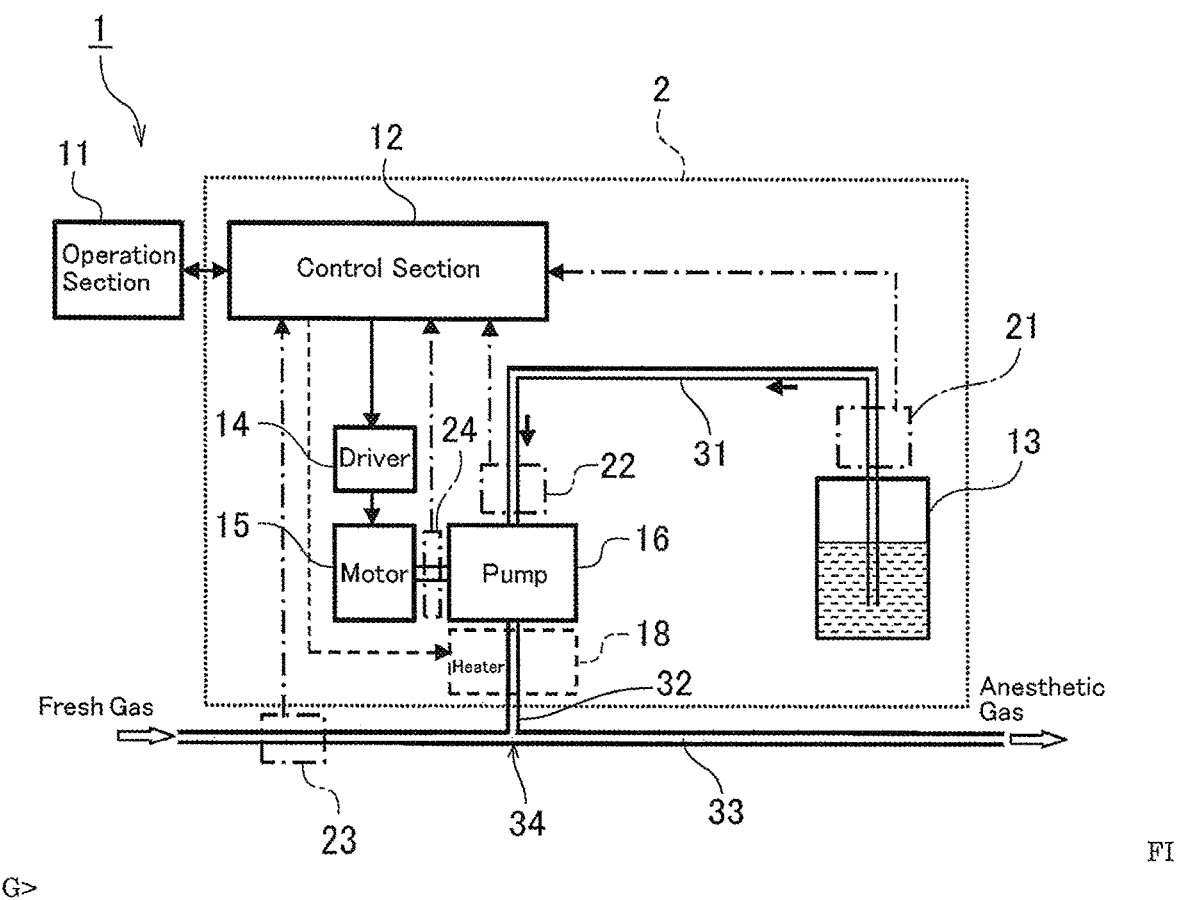
FIG. 2 is a block diagram showing the driving apparatus for the metering pump according to the embodiment of the present invention, a vaporizer and an anesthesia apparatus.

Next, a description will be given about a vaporizer 2 provided with the driving apparatus for the metering pump 16, and an anesthesia apparatus 1 provided with the vaporizer 2. FIG. 2 is a block diagram showing the driving apparatus for the metering pump 16 according to the embodiment of the present invention, the vaporizer 2 and the anesthesia apparatus 1.

In FIG. 2, the vaporizer 2 includes a control section 12, an anesthetic agent bottle 13, the motor driver 14, the stepping motor 15, the metering pump 16, a heater 18, an anesthetic-agent identifying sensor 21 and an anesthetic-agent flow-rate sensor 22.

The anesthesia apparatus 1 is configured by adding an operation section 11 and a fresh-gas flow-rate sensor 23 to the vaporizer 2. In the configuration of the anesthesia apparatus 1, the component elements for producing a fresh gas equivalent to a mixture of oxygen, a nitrous oxide and air are identical to those of a conventional anesthesia apparatus and hence are omitted.

An anesthetic agent stored in the anesthetic agent bottle 13 is sent through an anesthetic-agent flow path 31 to the suction port 16E of the metering pump 16. A fresh gas is supplied through a gas pipe line 33. The anesthetic agent discharged from the metering pump 16 flows through a flow path 32 and reaches to a junction point 34 thereof with the gas pipe line 33 for transferring the fresh gas. Around the flow path 32, the heater 18 is arranged, and the discharged anesthetic agent is vaporized by the heater 18 while being sent through the flow path 32, and then, is supplied to the gas pipe line 33.

The vaporizer 2 does not include a vaporizing chamber. The flow path 32, the heater 18 and the gas pipe line 33 are substituted for a conventional vaporizing chamber. Specifically, the anesthetic agent is almost completely vaporized by the heater 18 while being transferred through the flow path 32, and is supplied to the gas pipe line 33. Then, the anesthetic agent is mixed with the fresh gas inside of the gas pipe line 33 and is outputted as an anesthetic gas.

The operation section 11 is embodied by, for example, a display panel or the like and is a user interface for executing the initialization and change of the concentration of the anesthetic gas and the flow rate of the fresh gas. On a display screen thereof, necessary information on respiratory waveforms, set values, measured values, the concentration of oxygen and the like is indicated so that those pieces of information can be checked.

The anesthetic agent bottle 13 has a collar (ring) fitted thereon for identifying an anesthetic agent (such as halothane, ethrane, isoflurane and sevoflurane). A bottle adapter for each collar is attached to the anesthetic agent bottle 13, and then, the anesthetic agent bottle 13 is attached to the body of the anesthesia apparatus 1. The adapter has a code for each anesthetic agent, and the code is read by the anesthetic-agent identifying sensor 21 and sent to the control section 12. The anesthetic-agent flow-rate sensor 22 monitors whether an anesthetic agent exists inside of the piping which extends from the anesthetic agent bottle 13 through the anesthetic-agent flow path 31 to the suction port 16E of the metering pump 16.

Next, the control section 12 is embodied by a processor such as a CPU, has functions as macro-function programs in a memory thereof and executes the functions in the processor.

The control section 12 receives identification information from the anesthetic-agent identifying sensor 21 and decides which type the anesthetic agent is. Upon receiving an anesthetic gas concentration which is set in the operation section 11, the control section 12 calculates a required volume of an anesthetic gas (gaseous matter) on the basis of the set value of the anesthetic gas concentration and a fresh-gas flow rate detected by the fresh-gas flow-rate sensor 23. On the basis of Avogadro's law, the control section 12 converts the volume of the anesthetic gas (gaseous matter) into a volume of an anesthetic agent (liquid matter) and calculates a volume of the liquid delivered per unit time from the metering pump 16.

Specifically, the delivered liquid volume per unit time is calculated in the following formula (4).

Delivered liquid flow rate [mL/min]=Required anesthetic-gas flow rate [L/min]/Cubic volume of vaporized 1-mL anesthetic agent [L] (4)

Here, the numerator and the denominator in the right-hand side of the formula (4) are calculated in the formulas (5) and (6) respectively.

Required anesthetic-gas flow rate [L/min]=Set anesthetic-gas concentration value×Fresh-gas flow rate [L/min]/(1−Set anesthetic-gas concentration value) (5)

Cubic volume of vaporized 1-mL anesthetic agent [L]=22.4×(273+20)/273/Molecular weight×Specific gravity (6)

Next, in order to discharge the thus-calculated delivered liquid volume (anesthetic agent volume) per unit time from the metering pump 16, a suction and discharge cycle T [sec] of the metering pump 16 is calculated. Specifically, "the delivered liquid volume per unit time" is divided by "the discharge volume per stroke of the metering pump 16" to calculate the number of revolutions per minute [rpm] of the metering pump 16. Hence, the suction and discharge cycle T [sec] of the metering pump 16 is calculated by 60 [sec]/the number of revolutions [rpm] of the metering pump 16.

On the basis of the calculated cycle T [sec] of the metering pump 16, a decision is made as to whether the revolution speed of the metering pump 16 (stepping motor 15) is relatively low (whether the effect of a pulsation in the metering pump 16 appears conspicuously upon the anesthetic gas concentration).

Specifically, the calculated cycle T is compared with a cycle threshold T MIN determined by the specifications of the stepping motor 15. If the calculated cycle T is equal to or more than the cycle threshold T MIN, then the decision is made that the revolution speed of the metering pump 16 (stepping motor 15) is relatively low. In this case, within the cycle T, the discharge period T2 is set to be longer than the suction period T1, and during the discharge period T2, the stepping motor 15 revolves in a sinusoidal form, thereby keeping constant the travelling speed of the plunger 16A (which is below called a variable relative-comparison mode). Accordingly, the discharge flow rate of the metering pump 16 is kept substantially constant, so that a pulsation can be suppressed.

On the other hand, if the calculated cycle T is less than the cycle threshold T MIN, then the decision is made that the revolution speed of the metering pump 16 (stepping motor 15) is relatively high and hence the effect of a pulsation in the metering pump 16 is slight. In this case, within the cycle T, the suction period T1 and the discharge period T2 are each set to T/2 in the same way as a conventional setting. Then, the stepping motor 15 is revolved at a constant speed, thereby leading the plunger 16A to make a sinusoidal reciprocating motion (which is below called a constant revolution mode).

The cycle threshold T MIN is set on the basis of a set maximum speed Fs [pps] based upon a maximum self-starting frequency fs [rpm] of the stepping motor 15. In the variable relative-comparison mode, control is executed such that the interval between drive pulses is variable within the period when the stepping motor 15 makes half a revolution. This control requires a self-starting operation (instantaneous starting and stopping operation without an acceleration/deceleration time: rectangular drive). The self-starting operation is feasible only within a lower speed range (self-starting range) than the maximum self-starting frequency Fs [pps]. In contrast, within a higher speed range than the speed of the self-starting range, an acceleration and deceleration operation (pulse-speed gradually heightening (lowering) operation with an acceleration/deceleration time: trapezoidal drive) is executed, so that the variable relative-comparison mode cannot be set within the higher speed range.

Figure 3A:
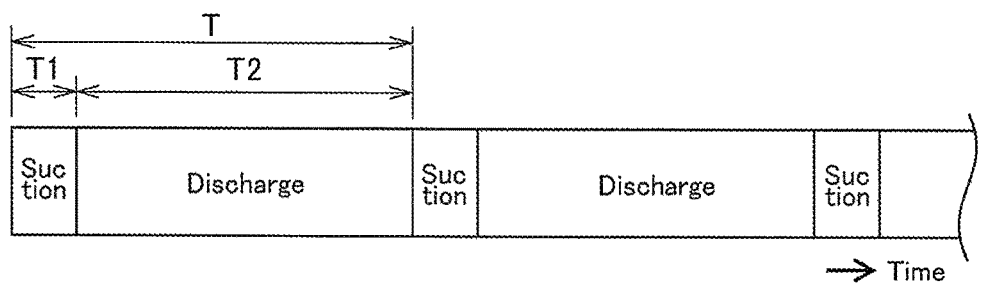
FIGS. 3(a) to 3(e) are time charts showing drive control in a driving method and the driving apparatus for the metering pump according the embodiment of the present invention.
Figure 3B:
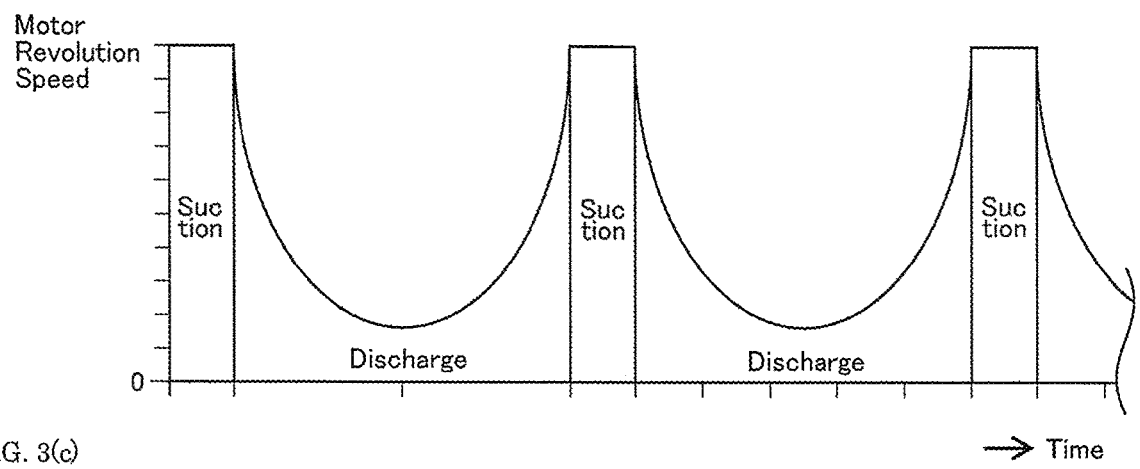
Figure 3C:
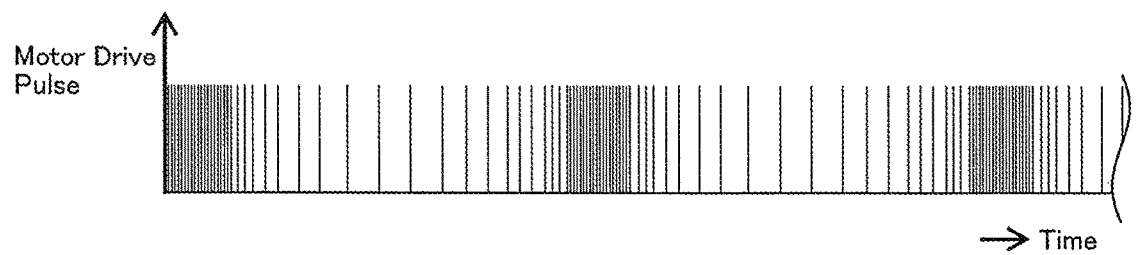
Figure 3D:
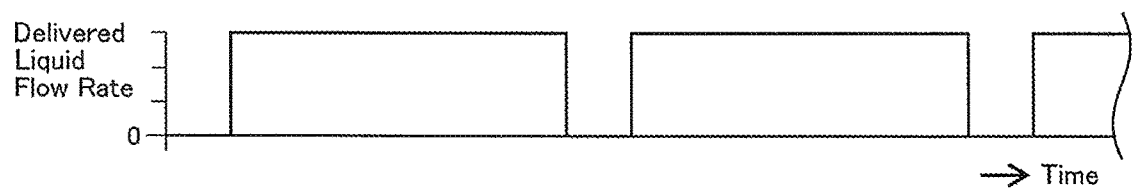

Next, driving control of the metering pump 16 in the anesthesia apparatus 1 or the vaporizer 2 will be described with reference to the time charts in the variable relative-comparison mode of FIGS. 3(a) to 3(e). FIG. 3(a) shows the suction period and the discharge period of the metering pump 16; FIG. 3(b), the revolution speed of the stepping motor 15; FIG. 3(c), the drive pulses supplied to the stepping motor 15 by the motor driver 14; FIG. 3(d), the delivered liquid flow rate (delivered liquid volume per unit time) by the metering pump 16; and FIG. 3(e), the anesthetic gas concentration.

First, as shown in FIG. 3(a), in the variable relative-comparison mode, within the cycle T [sec] of the metering pump 16, the discharge period T2 is set to be longer than the suction period T1. Specifically, during the suction period T1, control is executed such that the stepping motor 15 revolves at a constant speed or at the set maximum speed Fs [pps]. The number of pulses Np necessary for the suction period T1 is "Np=π/step angle", and hence, the suction period T1 [sec] is calculated in the formula T1=Np/Fs. On the other hand, the discharge period T2 [sec] is calculated in the formula T2=T−T1.

In addition, in the variable relative-comparison mode, as shown in FIG. 3(b), control is executed such that the stepping motor 15 revolves at a constant speed during the suction period T1, while control is executed such that the stepping motor 15 revolves at variable speeds in a sinusoidal form during the discharge period T2.

Hence, as shown in FIG. 3(c), the motor driver 14 supplies drive pulses at a pulse interval of "T1/Np" during the suction period T1, while it supplies drive pulses at pulse intervals calculated in the formulas (2) and (3) during the discharge period T2.

As described above, the stepping motor 15 revolves in a sinusoidal form during the discharge period T2, thereby keeping constant the travelling speed of the plunger 16A. Therefore, as shown in FIG. 3(d), the delivered liquid flow rate (discharged liquid volume per unit time) by the metering pump 16 is kept constant, thereby suppressing a pulsation in the metering pump 16.

Figure 3E:
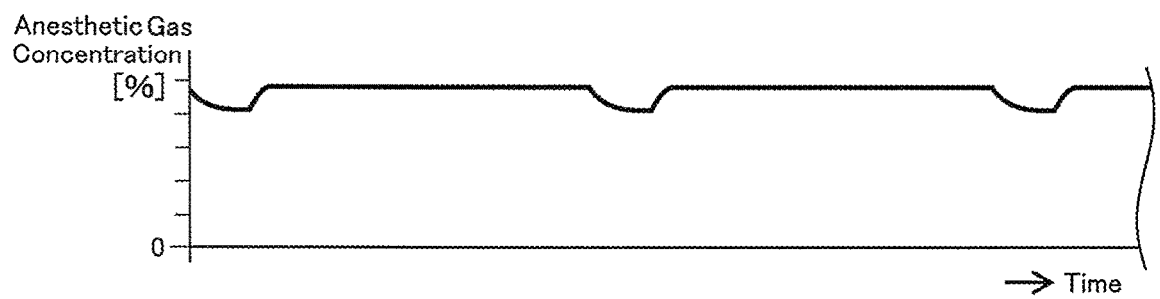

Specifically, as shown in FIG. 3(e), the anesthetic gas concentration falls slightly during the suction period T1 when the metering pump 16 stops delivering the liquid. However, the suction period T1 is shortened to the utmost, and further, the temporary variation in the anesthetic gas concentration is smoothed by the flow path 32, the heater 18 and the gas pipe line 33, thereby extremely reducing the effect of the pulsation on the temporary variation in the anesthetic gas concentration.

Figure 4:
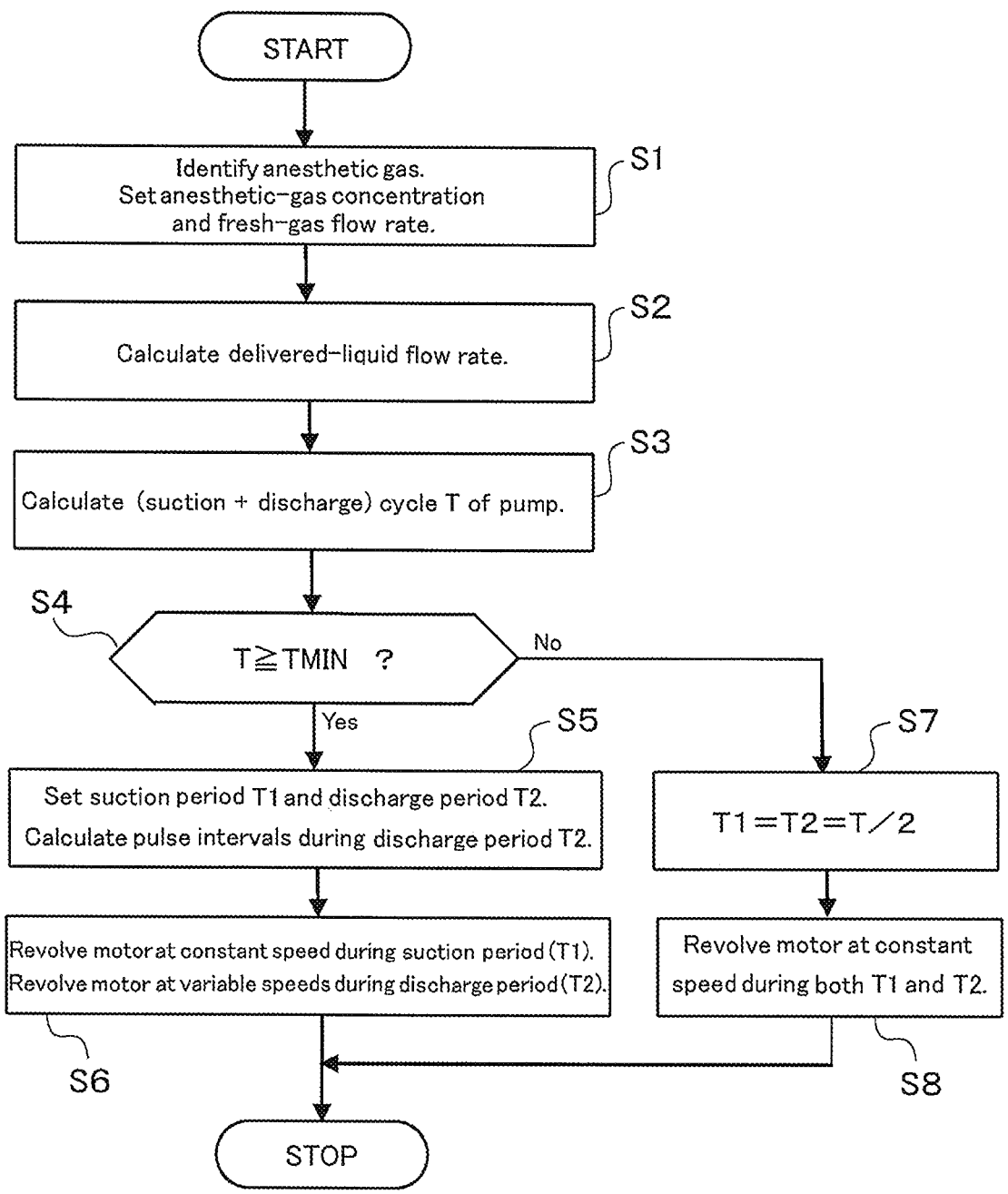
FIG. 4 is a flow chart showing the driving method for the metering pump according to the embodiment of the present invention.
Figure 5A:
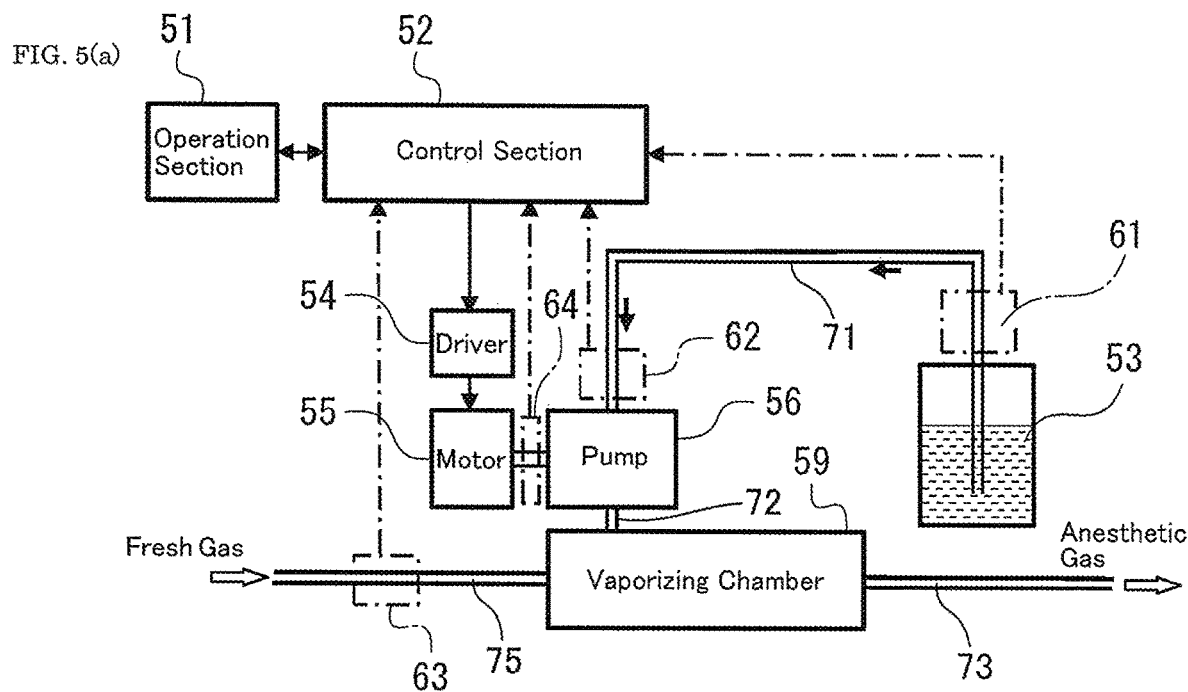
FIG. 5(a) is a block diagram showing a conventional anesthesia apparatus.
Figure 5B:
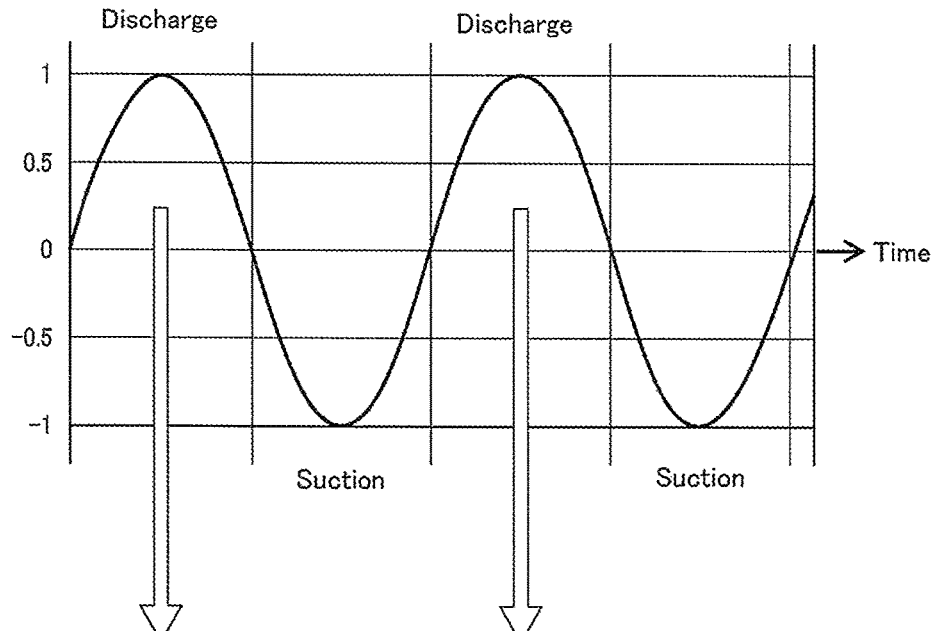
FIGS. 5(b) and 5(c) are time charts showing a pulsation in the anesthesia apparatus.
Figure 5C:
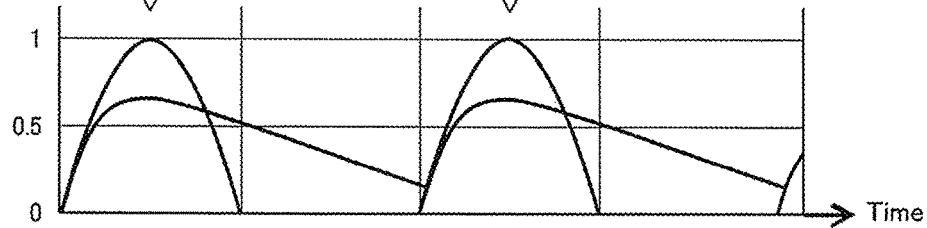
Figure 6A:
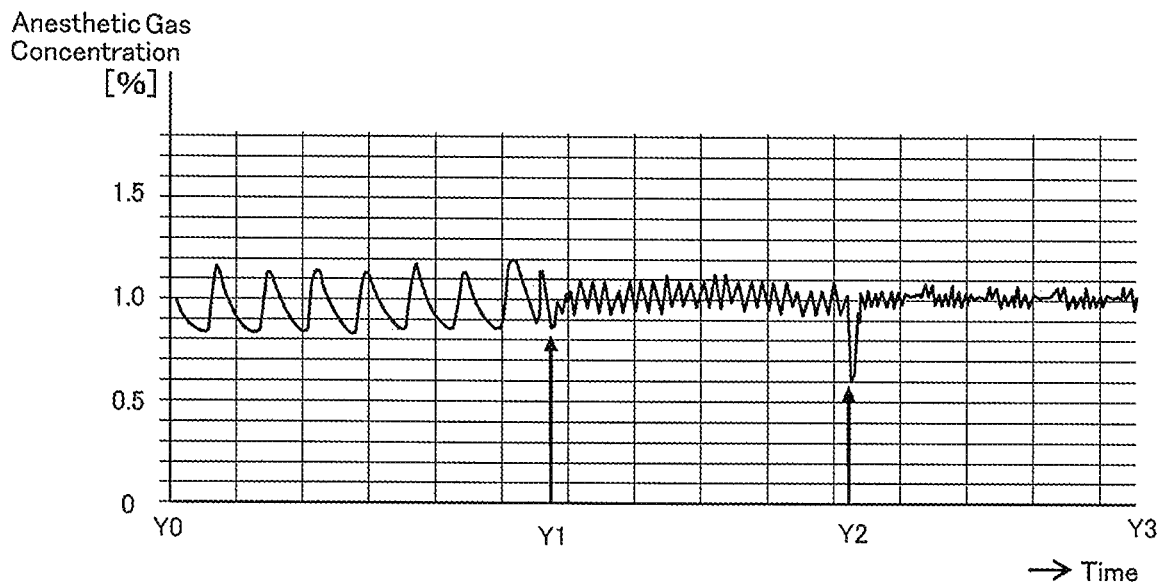
FIGS. 6(a) to 6(c) are time charts showing a pulsation, a time lag, and an overshoot and an undershoot respectively in the conventional anesthesia apparatus.
Figure 6B:
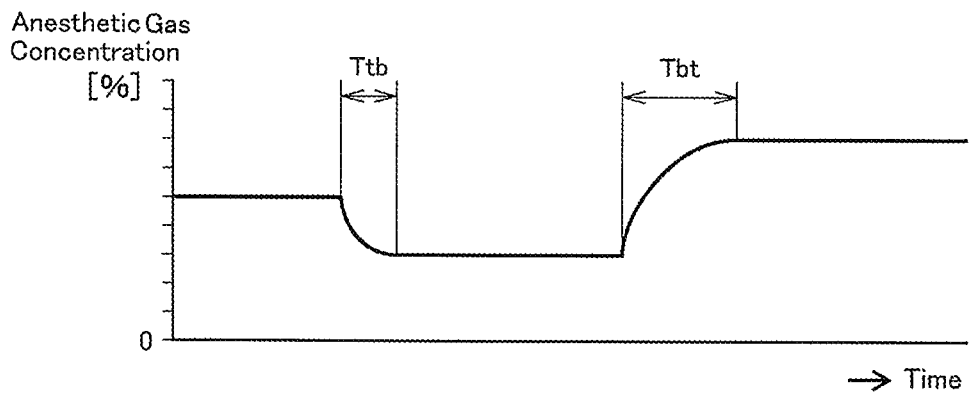
Figure 6C:
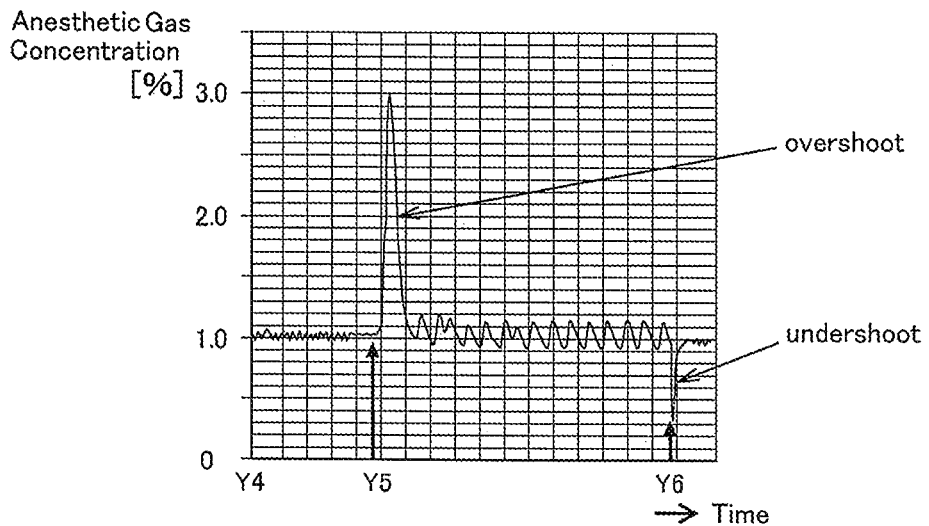

Next, a driving method for the metering pump 16 in the anesthesia apparatus 1 or the vaporizer 2 will be described with reference to FIG. 4.

First, in a step S1, the control section 12 receives identification information from the anesthetic-agent identifying sensor 21 and decides which type the anesthetic agent is. Upon receiving an anesthetic gas concentration which is set in the operation section 11 and information on a fresh-gas flow rate detected by the fresh-gas flow-rate sensor 23, the control section 12 sets the set value of the anesthetic gas concentration and the fresh-gas flow rate respectively.

In a step S2, on the basis of the set anesthetic-gas concentration value and the fresh-gas flow rate, the control section 12 calculates a required volume of an anesthetic gas (gaseous matter) in the formula (5). On the basis of Avogadro's law, the control section 12 converts the volume of the anesthetic gas (gaseous matter) into a volume of an anesthetic agent (liquid matter) in the formula (6) and calculates a volume of the liquid delivered per unit time from the metering pump 16 in the formula (4).

A detailed description will be given using specific numerical values as an example. As the metering pump 16, a conventional pump is employed: a constant delivery pump STH model by Fluid Metering Inc. which is adjusted to 5 [µL/stroke]; the set range of revolution speed=0 to 600 [rpm] (3 [mL/min]). As the stepping motor 15, a motor of the PK series: PK244-02B is employed. The step angle is 1.8 [°/pulse], and the number of pulses Np necessary for the suction period T1 or the discharge period T2 is calculated in the formula Np=π/step angle=100 [pulse].

In addition, as the anesthetic agent, sevoflurane is employed, and the set anesthetic-gas concentration value is 1.0[%] and the fresh-gas flow rate is 0.5 [L/min]. Into the formulas (5), (6) and (4), the molecular weight=200.1 and specific gravity=1.52 of sevoflurane is substituted, and hence, the delivered liquid volume per unit time becomes 0.0275 [mL/min].

In a step S3, in order to discharge the calculated delivered liquid volume (anesthetic agent volume) per unit time from the metering pump 16, the control section 12 calculates the suction and discharge cycle T [sec] of the metering pump 16.

In the specific example, "the delivered liquid volume per unit time=0.0275 [mL/min]" is divided by "the discharge volume per stroke of the metering pump 16=5 [µL/stroke]", and thereby, the number of revolutions per minute of the metering pump 16 becomes 5.5 [rpm]. Hence, the suction and discharge cycle T [sec] of the metering pump 16 is calculated in the formula T=60 [sec]/5.5 [rpm]=10.9 [sec].

Next, in a step S4, the control section 12 decides whether the cycle T [sec] of the metering pump 16 is equal to or more than the cycle threshold T MIN.

In the variable relative-comparison mode, the control section 12 sets, within the cycle T of the metering pump 16, the discharge period T2 to be longer than the suction period T1. The suction period T1 is set to the shortest period which is determined by a self-starting frequency. Preferably, it may be set to be equal to or less than a quarter to one third of the discharge period T2. In the specific example, the maximum self-starting frequency Fs of the stepping motor 15 is set to 500 [pps], and hence, the suction period T1 is calculated in the formula T1=Np/Fs=100/500=0.2 [sec]. On the other hand, the discharge period T2 is set to 0.6 [sec] which is three times longer, and hence, the cycle threshold T MIN in the variable relative-comparison mode becomes 0.8 [sec] in total. In the specific example, if the cycle T [sec] of the metering pump 16 is equal to or more than the cycle threshold T MIN, then the process goes to a step S5 for the variable relative-comparison mode.

In the step S5 (variable relative-comparison mode), in the specific example, as described above, the suction period T1 is 0.2 [sec] while the discharge period T2 is calculated in the formula T2=T−T1=10.9−0.2=10.7 [sec]. Then, the control section 12 sets the pulse interval during the suction period T1 to 2 [msec], and in the formula (3), calculates timings for supplying drive pulses during the discharge period T2.

In a step S6 (variable relative-comparison mode), the control section 12 supplies drive pulses at a pulse interval of 2 [msec] during the suction period T1, and thereby, allows the stepping motor 15 to revolve at a constant speed. On the other hand, it supplies drive pulses at the supplying timings calculated in the formula (3) during the discharge period T2, and thereby, allows the stepping motor 15 to revolve at variable speeds (in a sinusoidal form).

As described above, in the variable relative-comparison mode, the stepping motor 15 revolves in a sinusoidal form during the discharge period T2, thereby keeping constant the travelling speed of the plunger 16A. Accordingly, the delivered liquid flow rate (discharge volume per unit time) of the metering pump 16 is kept constant, so that a pulsation in the metering pump 16 can be suppressed.

On the other hand, in the step S4, if the decision is made that the cycle T [sec] of the metering pump 16 is less than the cycle threshold T MIN, then the process goes to a step S7 for the constant revolution mode which is the same as a conventional operation. For example, if the cycle T is 0.4 [sec], then the suction period T1 and the discharge period T2 are each set to T/2=0.2 [sec](step S7). During both the suction period T1 and the discharge period T2, drive pulses are supplied at a pulse interval of 2 [msec], and thereby, the stepping motor 15 revolves at a constant speed. The metering pump 16 (stepping motor 15) revolves at a relatively high speed, and hence, the effect of a pulsation in the metering pump 16 is slight.

As described hereinbefore, in the driving method for the metering pump 16, and the driving apparatus for the metering pump 16 according to this embodiment of the present invention, and the vaporizer 2 and the anesthesia apparatus 1, the control section 12 calculates the suction and discharge cycle T of the metering pump 16 on the basis of a set anesthetic-gas concentration and a fresh-gas flow rate, and within the cycle T, sets the discharge period T2 to be longer than the suction period T1. Therefore, the suction period T1 when no discharge is given is shortened to the utmost, thereby suppressing a fall in the anesthetic gas concentration. Further, the revolution speed of the stepping motor 15 is controlled so that the travelling speed of the plunger 16A is kept constant during the discharge period T2. Therefore, the discharge flow rate of the metering pump 16 is kept substantially constant, thereby suppressing a pulsation in the metering pump 16. As a result, a vaporizing chamber conventionally necessary for suppressing the pulsation is dispensable, thereby making it feasible to suppress a pulsation in the metering pump 16 without increasing the cubic volumes of the vaporizer 2 and the anesthesia apparatus 1, and to lower the costs and reduce the sizes of the vaporizer 2 and the anesthesia apparatus 1. Still further, since a vaporizing chamber is unnecessary, a time lag will not arise when the set anesthetic-gas concentration has been changed, and an overshoot or undershoot in the anesthetic gas concentration will not arise when the fresh-gas flow rate has been sharply changed.

Although the embodiment of the present invention has been above described, the present invention is not limited to the embodiment as a specific configuration thereof.

For example, in the specific example, a constant delivery pump STH model by Fluid Metering Inc. which is adjusted to 5 [µL/stroke] is employed as the metering pump 16. The present invention is capable of suppressing a pulsation in the metering pump 16 while revolving at a low speed, so that the volume per stroke may be increased. For example, if it is adjusted to 20 [µL/stroke], then the delivered liquid flow rate is quadrupled at the same number of revolutions per unit time.

The metering pump 16 having a larger volume per stroke has other advantages: first, a preparation for starting and a preparation for termination can be made in a shorter time; second, the practical setting range is widened so that a higher flow rate/a higher concentration can be set; third, the number of revolutions per unit time can be decreased at the same delivered liquid flow rate, thereby lengthening the lifetime of the metering pump 16; and fourthly, the pressure resistance (back-pressure value against which the constant-delivery performance can be maintained) is enhanced (up to 0.7 [MPa] from the present 0.3 [MPa]), thereby enabling a liquid delivery to a pressurized container.

Furthermore, in the above embodiment, timings for supplying drive pulses during the discharge period T2 are calculated in the formula (3), and then, the drive pulses are supplied to the stepping motor 15. However, the drive pulses may be individually supplied at each calculated pulse interval. In this case, in the formula (3), the pulse interval between the (k−1)th drive pulse and the (k)th drive pulse is expressed as "π sin(kπ/Np)/Np·Vp". Hence, the (k−1)th drive pulse is supplied, and after an elapse of the pulse interval "π sin(kπ/Np)/Np·Vp", the (k)th drive pulse may be supplied.

DESCRIPTION OF THE SYMBOLS

1: anesthesia apparatus
2: vaporizer
11: operation section
12: control section
13: anesthetic agent bottle
14: motor driver
15: stepping motor (motor)
16: metering pump
16A: plunger
16B: notch portion
16C: pin
16D: cylinder
17: crank
17A: bearing
18: heater
21: anesthetic-agent identifying sensor
22: anesthetic-agent flow-rate sensor
23: fresh-gas flow-rate sensor
31: anesthetic-agent flow path
32: flow path
33: gas pipe line

The invention claimed is:

1. A driving method for a metering pump for anesthesia which includes an eccentric mechanism connected to a motor, a plunger connected to the eccentric mechanism and capable of reciprocating along and rotating about a first axis within a cylinder, wherein the first axis is angled with respect to a revolution axis of the motor, wherein rotation of the motor causes the plunger to rotate about the first axis and reciprocate along the first axis, the method comprising:

rotating the motor to cause the plunger to rotate about the first axis and reciprocate along the first axis; and sucking in an anesthetic agent via a suction port in the cylinder during a suction period and discharging the anesthetic agent via a discharge port in the cylinder during a discharge period by driving the motor, wherein driving the motor causes the rotating motion and the reciprocating motion of the plunger and causes the opening and closing of the suction port and the discharge port of the metering pump via a notch formed in an end part of the plunger, wherein a variable relative-comparison mode is provided in which the discharge period of the metering pump is set to be longer than the suction period of the metering pump, and a revolution speed of the motor is controlled so that a travelling speed of the plunger along the first axis is kept constant during the discharge period, wherein if a revolution speed of the motor is determined to be equal to or less than a predetermined value, then the variable relative-comparison mode is utilized, and if a revolution speed of the motor is determined to be more than the predetermined value, then a constant revolution mode is utilized in which the suction period of the metering pump is set to be equal to the discharge period of the metering pump and the motor is set to make a constant revolving motion during the suction period and the discharge period.

2. A driving apparatus for a metering pump, comprising:
a motor;
a control section configured to control a rotation of an output section of the motor about a revolution axis; and
a metering pump for anesthesia joined to the motor, the metering pump including an eccentric mechanism connected to a plunger capable of reciprocating along and rotating about a first axis within a cylinder, wherein the first axis is angled with respect to the revolution axis of the motor, wherein the rotation of the output section causes the plunger to rotate around the first axis and reciprocate along the first axis, wherein the metering pump is capable of sucking in an anesthetic agent via a suction port in the cylinder during a suction period and discharging the anesthetic agent via a discharge port in the cylinder during a discharge period by driving the motor, wherein driving the motor causes the rotation motion and the reciprocating motion of the plunger and causes the opening and closing of the suction port and the discharge port of the metering pump via a notch formed in an end part of the plunger, wherein the control section is capable of controlling the motor during a variable relative-comparison mode so that the discharge period of the metering pump is set to be longer than the suction period of the metering pump, and a revolution speed of the motor is controlled so that a travelling speed of the plunger along the first axis is kept constant during the discharge period wherein the control section utilizes the variable relative-comparison mode if a revolution speed of the motor is determined to be equal to or less than a predetermined value; and if a revolution speed of the motor is determined to be more than the predetermined value, the control section utilizes a constant revolution mode in which the suction period of the metering pump is set to be equal to the discharge period of the metering pump and the motor is set to make a constant revolving motion during the suction period and the discharge period.

3. The driving apparatus for the metering pump according to claim 2, wherein:

the motor is a stepping motor which is controlled with a number (Np) of drive pulses within a rotation-angle range of 0 to π during the discharge period of the metering pump; and the control section supplies the (k)th (k=1 to Np) drive pulse to the stepping motor at a timing $t_k$ defined by the following formula:

$$t_k = \frac{\pi}{NpVp} \sum_{m=1}^{k} \sin\left(\frac{m\pi}{Np}\right)$$

during the discharge period of the metering pump the reciprocating motion of the plunger is defined as Vp.

4. A vaporizer, comprising:

a motor;

a control section for controlling a revolution of an output section of the motor about a revolution axis;

a metering pump for anesthesia joined to the motor, the metering pump including:
  an eccentric mechanism connected to the output section of the motor;
  a cylinder having a suction port and a discharge port;
  a plunger connected to the eccentric mechanism and configured to reciprocate along and rotate about a first axis within the cylinder when the output section of the motor rotates about the revolution axis, wherein the first axis is angled with respect to the revolution axis of the motor, wherein the plunger has a notch at an end portion thereof, wherein the metering pump sucks in an anesthetic agent via the suction port during a suction period and discharges an anesthetic agent by rotating about the first axis and reciprocating along the first axis wherein the rotation of the piston about the first axis causes the notch to open and close the suction port and a discharge port of the metering pump, a gas pipe line configured for transferring a fresh gas; and a flow path connected to the gas pipe line, the flow path configured to deliver and vaporize a liquid discharged from the metering pump and supply the liquid to the gas pipe line, wherein the vaporizer provides a mixed gas comprised of the fresh gas and the vaporized liquid gas, wherein the control section includes a variable relative-comparison mode in which a discharge period of the metering pump is set to be longer than the suction period of the metering pump, and a revolution speed of the motor output section is controlled so that a travelling speed of the plunger along the first axis is kept constant during the discharge period, wherein the control section utilizes the variable relative-comparison mode if a revolution speed of the motor is determined to be equal to or less than a predetermined value; and if a revolution speed of the motor is determined to be more than the predetermined value, the control section utilizes a constant revolution mode in which the suction period of the metering pump is set to be equal to the discharge period of the metering pump and the motor is set to make a constant revolving motion during the suction period and the discharge period.

5. The vaporizer according to claim 4, wherein:

the motor is a stepping motor which is controlled with a number (Np) of drive pulses within a rotation-angle range of 0 to $\pi$ during the discharge period of the metering pump; and the control section supplies the (k)th (k=1 to Np) drive pulse at a timing tk defined by the following formula:

$$t_k = \frac{\pi}{NpVp} \sum_{m=1}^{k} \sin\left(\frac{m\pi}{Np}\right)$$

during the discharge period of the metering pump if the reciprocating motion of the plunger is defined as Vp.

6. The vaporizer according to claim 4, wherein:

a flow-rate sensor for detecting a flow rate of the fresh gas is provided, the flow-rate sensor being arranged before a junction place of the gas pipe line with the flow path in a transfer direction of the fresh gas; and the control section calculates a suction and discharge cycle of the metering pump on the basis of a set concentration of the mixed gas and a flow rate of the fresh gas detected by the flow-rate sensor.

7. An anesthesia apparatus, comprising the vaporizer according to claim 4, wherein the anesthesia apparatus outputs an anesthetic gas, the anesthetic gas being a mixed gas of the fresh gas containing at least oxygen and an anesthetic agent gas subjected to vaporization.

\* \* \* \* \*